United States Patent
Pauley

[11] Patent Number: 5,975,078
[45] Date of Patent: Nov. 2, 1999

[54] RESPIRATORY MONITORING APPARATUS

[76] Inventor: Randall O. Pauley, 15006 Lantern Creek La., Houston, Tex. 77068

[21] Appl. No.: 08/898,638

[22] Filed: Jul. 22, 1997

[51] Int. Cl.[6] .................................................. A61M 16/00
[52] U.S. Cl. ............................... 128/205.23; 128/205.13; 128/205.14; 128/203.12; 128/204.21
[58] Field of Search ........................ 128/205.23, 205.13, 128/205.17, 203.12, 202.22, 205.14, 205.15, 203.28, 205.16, 204.21; 600/484, 513, 728, 523, 529

[56] References Cited

U.S. PATENT DOCUMENTS

| | | | |
|---|---|---|---|
| 2,225,201 | 12/1940 | Anderson | 128/205.14 |
| 4,340,044 | 7/1982 | Levy et al | 128/204.24 |
| 4,981,139 | 1/1991 | Pfohl | 600/484 |
| 5,022,402 | 6/1991 | Schieberl et al. | 600/484 |
| 5,299,579 | 4/1994 | Gedeon et al. | 128/205.15 |
| 5,320,093 | 6/1994 | Raemer | 128/203.12 |
| 5,497,767 | 3/1996 | Olsson et al. | 128/205.13 |
| 5,647,352 | 7/1997 | Niemi et al. | 128/205.13 |
| 5,662,099 | 9/1997 | Tobia et al. | 128/205.13 |
| 5,664,563 | 9/1997 | Schroeder et al. | 128/205.13 |

*Primary Examiner*—John G. Weiss
*Assistant Examiner*—V. Srivastava
*Attorney, Agent, or Firm*—Bill B. Berryhill

[57] ABSTRACT

Apparatus for monitoring respiration of a patient being ventilated through a flexible gas reservoir of an anesthesia machine. The flexible reservoir is provided with electrical components for generating an electrical signal which varies in response to movement of opposing sides of the reservoir closer to or farther from each other. Sound generating apparatus receives the electrical signal producing an audible sound the pitch and volume of which varies in response to the distance between opposing sides of the reservoir.

8 Claims, 2 Drawing Sheets

RESPIRATORY MONITORING APPARATUS

BACKGROUND OF THE INVENTION

1. Field of the Invention

The present invention pertains to apparatus for monitoring respiration of an individual. More specifically, the present invention pertains to apparatus for monitoring respiration of a patient being ventilated through the flexible gas reservoir or bag of an anesthesia machine.

2. Description of the Prior Art

A typical anesthesia machine is provided with compressed gas containers, conduits, relief valves, pressure gauges, flow meters and filters. A face mask is connected by a Y-connection to two flexible conduits, one for inhalation and one for exhalation of the patient. Oxygen or other gases may be provided to the patient through the inhalation conduit and carbon dioxide may be exhaled from the patient through the exhalation conduit. The flexible bag or reservoir fills and empties as the patient is being ventilated. The patient can be ventilated by hand, with a mechanical ventilator or by spontaneous respiration. In spontaneous respiration the patient breathes on his own. In respiration by hand, the flexible reservoir or bag is squeezed during inhalation and released during exhalation. With a mechanical ventilator, the reservoir bag is by=passed to an electrical or pneumatic ventilator.

If the person monitoring the respiration of the patient, usually an anesthesiologist, is near the gas reservoir or breathing bag, he/she can tell by visual observation or feel whether or not the patient's lungs are being ventilated in a satisfactory manner. However, it is not always possible to feel or visually observe the flexible gas reservoir or breathing bag.

In a number of cases, it may be necessary for the anesthesiologist to be located some distance from the patient. For example, the anesthesiologist may need to be out of the operating suite while a patient is undergoing general anesthesia for an MRI (magnetic resonance imaging) procedure. The anesthesiologist may be required to be away from the patient undergoing X-ray or CAT-scan examination to whom general anesthesia has been administered to prevent movement of the patient. This may be required for neonates, infants, children and adults, including confused or disoriented patients. Patients undergoing X-ray therapy for tumors and other specifically located tumors may require general anesthesia for absolute non-movement. In these cases, the anesthesiologist would not be allowed to be near the patient. In other situations, intra-operative X-ray therapy may be given directly to tumors in operating rooms, requiring all personnel to leave the operating suite while the patient is under anesthesia for the X-ray therapy treatment.

Of course the primary purpose of monitoring the respiration of a patient is to make sure proper lung ventilation is taking place and that apnea (an arrest of respiration) does not occur. Apnea or unusual respiratory oxygen changes can be due to laryngospasm, bronchospasm, drug, mechanical, or physiologically induced pulmonary changes, cardiac arrest, malposition of the laryngeal mask airway or aspiration.

To detect apnea and other respiratory problems, most patients placed under general anesthesia are presently monitored with a pulse oximeter. The oximeter utilizes a sensor peripherally attached to some part of the patient's anatomy, e.g. finger, toe or ear lobe. When oxygen decreases to an unacceptable level, the oximeter so indicates allowing the anesthesiologist to take measures to restore proper ventilation. However, with administration of oxygen (typically 50% to 100%) during an anesthetic the pulmonary oxygen saturation level may remain high, due to oxygen super saturation, for two or three minutes after apnea or other respiratory problems occur. By the time the oximeter indicates an oxygen problem, the anesthesiologist must move very quickly to correct the problem. If the oximeter is not properly positioned or the anesthesiologist is slow in reacting, a potentially harmful situation may arise.

Obviously, any improvement in recognizing apnea or oxygen problems more quickly would be desirable. If detection of such problems could occur two or three minutes earlier, it might result in reduction of respiratory problems, including possible death.

SUMMARY OF THE PRESENT INVENTION

The present invention provides apparatus for monitoring respiration of a patient being ventilated through a flexible gas reservoir of an anesthesia machine. The flexible reservoir or breathing bag of the machine is provided with means for generating an electrical signal which varies in response to movement of the sides of the reservoir, during ventilation of a patient, closer to or farther from each other. The means for generating an electrical signal is connected to sound generating means which produces an audible sound, the pitch, quality, and volume of which varies in response to the distance between the sides of the gas reservoir. Thus, sound emitted by the sound generating means will vary in pitch, quality and volume during the ventilation cycle. For example, during inhalation the sound will increase in pitch and volume. during exhalation the sound will diminish in pitch and volume. The respiration rate can be easily determined by the expiration of time between the lowest pitch and the highest pitch emitted by the sound producing device.

Thus, immediate identification of respiration rate, lung volume and apnea can be recognized at the patient's side or some remote distance therefrom. This allows monitoring even if the anesthesiologist is away from the patient for any reason whatsoever. It also allows immediate attention to a respiratory problem and as many as two or three minutes prior to indication of such problems by pulse oximeters. Many other objects and advantages of the invention will be apparent from reading the description which follows in conjunction with the accompanying drawings.

DESCRIPTION OF A PREFERRED EMBODIMENT OF THE INVENTION

Figure 1:
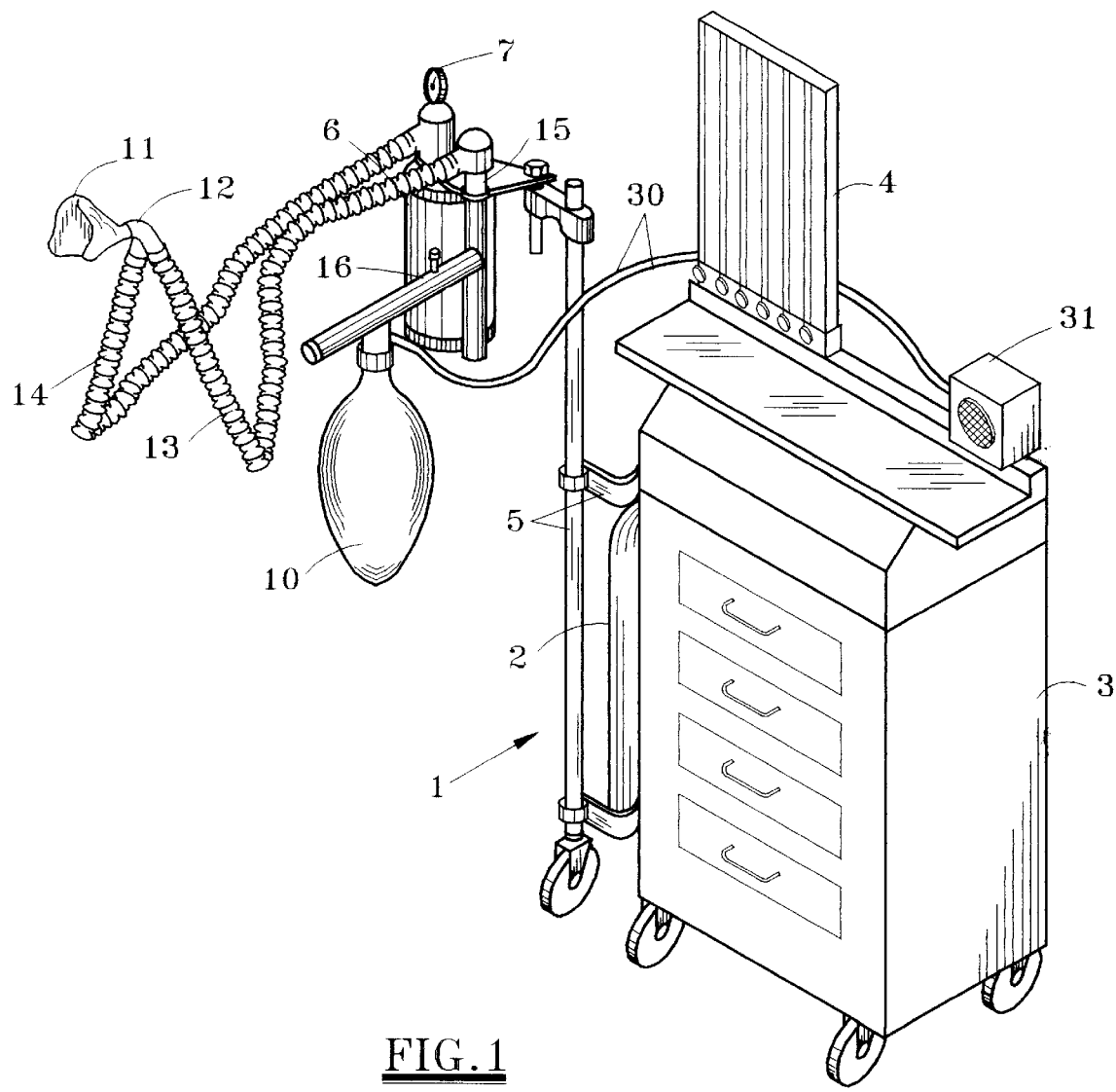
FIG. 1 is a pictorial representation of an anesthesia gas machine utilizing a flexible gas reservoir or breathing bag according to a preferred embodiment of the invention.

Referring first to FIG. 1, there is shown an anesthesia gas machine 1 provided with one or more bottles 2 of oxygen or other anesthetic inhalation agents. A cabinet 3 on wheels may support flow meters 4 and various structural members 5 for supporting a gas filter 6, pressure gauge 7 and flexible gas reservoir or breathing bag 10.

A face mask 11 is connected through a Y-piece 12 to flexible tubes or hoses 13 and 14. The inhalation tube or hose 13 is connected through conduits 15 and 16 to a flexible gas reservoir or breathing bag 10. The exhalation tube 14 or hose is connected to the gas filter 6. A relief valve 7 and other customary valves (not shown) are provided for the anesthesiologist to control gas pressures and volumes.

The gas machine 1 may also support sound producing means 31 which may be connected, via electrical wiring 30, to electrical components (not shown) disposed in the breathing bag 10. These components will be more fully described hereafter.

The flexible gas reservoir or breathing bag 10 is ordinarily made of rubber or some other elastomeric material. The bag fills or expands with oxygen or other inhalation anesthetics while the patient is exhaling through the exhalation tube 14. The bag 10 empties or deflates as the oxygen or other gas therein is drawn through the inhalation tube 13 and the face mask 11. Carbon dioxide exhaled through the exhalation tubing 14 is filtered through the filter canister 6.

Figure 2:
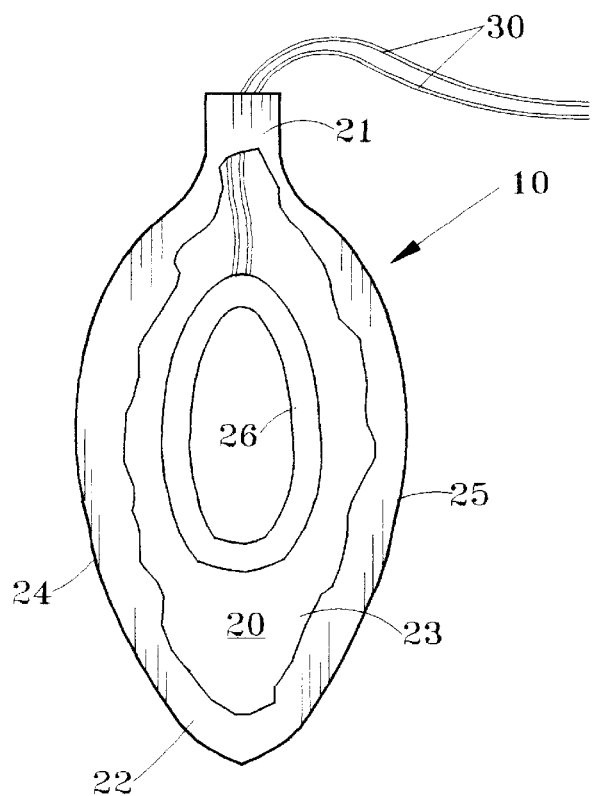
FIG. 2 is a front view of a flexible gas reservoir, a portion of which has been cut away to reveal internal elements of an improved reservoir according to a preferred embodiment of the invention.
Figure 3:
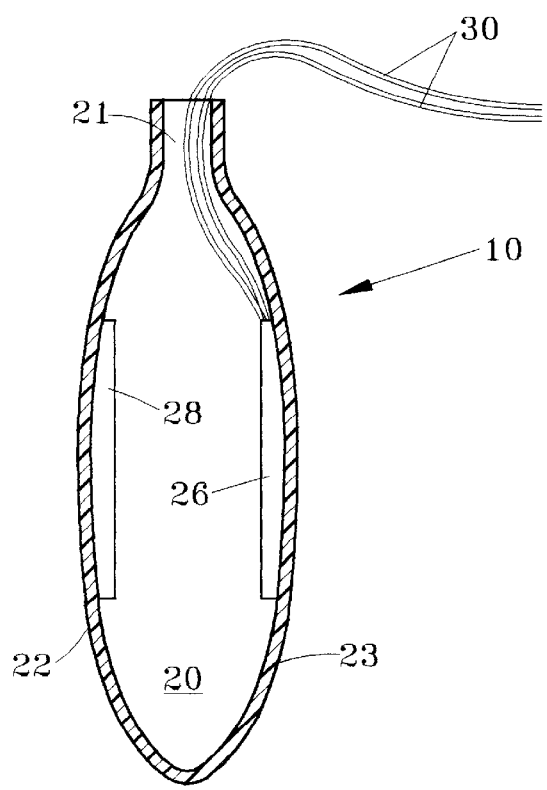
FIG. 3 is a side view, in section, of the flexible gas reservoir of FIG. 2, according to a preferred embodiment of the invention.

As best seen in FIGS. 2 and 3 the breathing bag 10 is typically manufactured of rubber or other flexible materials with a large expandable gas cavity 20 connectable through a small opening neck 21 and the conduits 15, 16 (see FIG. 1) with a source of oxygen or other inhalation agents and with inhalation tubing 13 (see FIG. 1) for communication with the patient being ventilated through an anesthesia gas machine. Most bags are manufactured so that the cavity 20 is formed between a pair of large sides 22, 23 and connecting edges 24, 25. As the cavity 20 is filled with oxygen, the bag 10 expands and the sides 22 and 23 move away from each other. This occurs during the exhalation phase of the respiration cycle while the patient exhales through the exhalation tubing 14. Once the bag is fully expanded and the patient begins to inhale oxygen from the bag 10, through inhalation tubing 13, the bag 10 begins to empty and contract, the sides 22 and 23 moving closer to each other.

In the present invention, the bag 10 is provided on the interior thereof, with means for generating an electrical signal which varies in response to movement of opposing sides 22, 23 of the bag closer to or farther away from each other. For example, as the sides 22, 23 move closer together the electrical signal becomes stronger, first indicating initiation, then time and volume of oxygen being inhaled by the patient. As the sides 22, 23 move farther apart the electrical signal becomes weaker, first indicating initiation and then time and volume of carbon dioxide being exhaled by the patient.

There are a number of ways of providing an electrical signal which varies in response to movement of the sides 22, 23 of the bag 10 closer to or farther away from each other. In the exemplary embodiment of FIGS. 2 and 3 one side 23 of the bag 10 is provided, on the interior thereof, with an electrical coil 26. The coil 26 is connected through wiring 30 to a pulse generator (not shown). The opposite side 22 of the bag 10 is provided with a metal plate 28 of some type.

A brief pulse of current is fed to the coil 26, through the wiring 30. This produces a magnetic field. The field enters the metal plate 28, inducing Eddy currents therein. These Eddy currents generate a magnetic field which, in turn, induces an opposite current in the then inactive coil 26. The current is detected by electronic components and transmitted to a sound generating device such as the speaker 31. The current generated by the magnetic field generated in the metal plate 28 will vary, typically becoming stronger when the sides 22, 23 of the bag 10 move closer together and becoming weaker when the sides 22, 23 of the bag 10 move farther apart.

Although the coil 26 and metal plate 28 are shown on the interior of bag 10, they could be disposed, in some manner, on the exterior of said bag. For example, they could be affixed to a shroud or cover (not shown) surrounding the bag 10.

The sound generator 31 could be of a number of types. For example, it could be a typical speaker in which current from the coil 26 would be transmitted to an amplifier coil (not shown) of the speaker 31. The speaker coil produces a magnetic field which induces vibrating in a thin cone or diaphragm of the loud speaker. Vibration of the cone or diaphragm produces an audible sound, the pitch, volume and quality of which will vary depending upon the strength of the current from the breathing bag coil 26 and the characteristics of the speaker. In general, the pitch and volume of the speaker would increase and decrease with movement of the bag sides 22, 23 closer to or farther from each other. If it is desired to prevent sound from disturbing the surgeon or other medical personnel, the speaker could be replaced with earphones to be worn by the anesthesiologist.

A single embodiment of the invention has been described herein. Many variations could be made without departing from the spirit of the invention. Other means of sensing movement of the bag sides and other means of producing audible signals could be easily devised. Accordingly, it is intended that the scope of the invention be limited only by the claims which follow.

I claim:

1. Apparatus for monitoring respiration of a patient spontaneously breathing through a flexible nonenclosed breathing bag of an anesthesia machine characterized in that said flexible breathing bag is provided with means for generating an electrical signal which varies in response to movement of opposing sides of said bag closer to or farther from each other, and further characterized by sound generating means connected to said electrical signal generating means for receiving said electrical signal, said sound generating means producing a continuously audible sound the pitch and volume of which varies with said electrical signal in response to the distance between said opposing sides of said bag.

2. Respiration monitoring apparatus as set forth in claim 1 in which said flexible breathing bag comprises an expandable and contractible bag having opposing sides which move farther away from each other upon an increase of gas volume therein and closer to each other upon a decrease of gas volume therein.

3. Apparatus for monitoring respiration of a patient spontaneously breathing through a flexible nonenclosed expandable and contractible breathing bag of an anesthesia machine characterized in that opposing sides of said breathing bag move farther away from each other upon an increase of gas volume therein and closer to each other upon a decrease of gas volume therein and comprising detector means attached to one of said opposing bag sides and generation means attached to the other of said opposing bag sides, said detector means and said generation means generating an electrical signal which varies in proportion to the distance between said opposing sides of said bag and further characterized by sound generating means connected to said detector means, said sound generating means producing a continuously audible sound the pitch and volume of which varies in response to the distance between said opposing sides of said bag.

4. Respiration monitoring means as set forth in claim 3 in which the electrical signal generated by said detector means and said generation means is connected through electrical wiring, to said sound generating means.

5. Respiration monitoring means as set forth in claim 4 in which said sound generating means includes a speaker audible to those in the vicinity of said anesthesia machine.

6. Respiration monitoring means as set forth in claim 4 in which said sound generating means includes earphones producing sounds audible only to the person wearing the earphones.

7. Respiration monitoring apparatus as set forth in claim 2 in which said means for generating an electrical signal comprises electrically conducting elements at each of said opposing sides of said flexible breathing bag, said elements producing an electrical signal the magnitude of which is dependent upon the distance between said opposing sides of said breathing bag.

8. Respiration monitoring apparatus as set forth in claim 7 in which said electrical signal is transmitted from at least one of said electrically conducting elements through electrical wiring to said sound generating means, said sound generating means producing an audible sound, the pitch and volume of which varies in response to the magnitude of said electrical signal.

* * * * *